(12) United States Patent
Marti et al.

(10) Patent No.: US 11,103,313 B2
(45) Date of Patent: Aug. 31, 2021

(54) REDUNDANT RECIPROCAL SURGICAL TRACKING SYSTEM WITH THREE OPTICAL TRACKERS

(71) Applicant: Atracsys Sarl, Puidoux (CH)

(72) Inventors: Gaëtan Marti, Le Mont-sur-Lausanne (CH); Maurice Hälg, Savigny (CH)

(73) Assignee: Atracsys Sarl, Puidoux (CH)

( * ) Notice: Subject to any disclaimer, the term of this patent is extended or adjusted under 35 U.S.C. 154(b) by 301 days.

(21) Appl. No.: 15/555,529

(22) PCT Filed: Mar. 4, 2016

(86) PCT No.: PCT/IB2016/051242
§ 371 (c)(1),
(2) Date: Sep. 4, 2017

(87) PCT Pub. No.: WO2016/139638
PCT Pub. Date: Sep. 9, 2016

(65) Prior Publication Data
US 2018/0049809 A1  Feb. 22, 2018

Related U.S. Application Data

(60) Provisional application No. 62/128,585, filed on Mar. 5, 2015.

(51) Int. Cl.
*A61B 34/20* (2016.01)
*A61B 34/30* (2016.01)
(Continued)

(52) U.S. Cl.
CPC ............. *A61B 34/20* (2016.02); *A61B 34/30* (2016.02); *A61B 90/37* (2016.02);
(Continued)

(58) Field of Classification Search
CPC .... A61B 2034/2055; A61B 2090/0818; A61B 2034/2057; A61B 34/20
See application file for complete search history.

(56) References Cited

U.S. PATENT DOCUMENTS

| 4,649,504 A | 3/1987 | Krouglicof et al. |
| 5,227,985 A | 7/1993 | De Menthon et al. |
| (Continued) | | |

FOREIGN PATENT DOCUMENTS

| DE | 10 2009 044642 | 5/2010 |
| WO | WO 2012/152264 | 11/2012 |
| WO | WO 2013/053397 | 4/2013 |

OTHER PUBLICATIONS

"Apex Robotic Technology: APEX Knee Surgical Navigation with the PRAXIM Robotic Cutting Guide", copyright by OMNIlife science, 2011, Rev 07/11, p. 46.
(Continued)

*Primary Examiner* — Serkan Akar
*Assistant Examiner* — Aminah Asghar
(74) *Attorney, Agent, or Firm* — Troutman Pepper Hamilton Sanders LLP

(57) ABSTRACT

The present invention relates to a redundant reciprocal tracking system composed of at least two trackers 10. A first tracker is able to sense partial or full pose data (orientation and position) of a second tracker in a first reference frame and the second tracker is able to sense partial or full pose data of the first tracker in a second reference frame. Pose data of first and second trackers are further transferred to a central processor 30, which is able to compute the transformation between first and second reference frame. Data generated by the trackers are such designed that they define an over-determined mathematical system (e.g. more than 6 degrees of freedom in a 3D setup). The over-determined information can be used to qualify and/or improve the
(Continued)

transformation of the reference frame. In an embodiment of the invention, the tracking system is an optical one and the over-determined information defines an error metric used to check the validity of the transformation. Such setup could be used in surgical navigation system in order to reduce the risk of injury or death of the patient.

15 Claims, 6 Drawing Sheets

(51) Int. Cl.
*A61B 17/00* (2006.01)
*A61B 90/00* (2016.01)
(52) U.S. Cl.
CPC ........... *A61B 2017/00221* (2013.01); *A61B 2034/2055* (2016.02); *A61B 2034/2057* (2016.02); *A61B 2090/0818* (2016.02); *A61B 2090/372* (2016.02); *A61B 2090/3983* (2016.02)

(56) References Cited

U.S. PATENT DOCUMENTS

| | | | | |
|---|---|---|---|---|
| 6,212,419 | B1* | 4/2001 | Blume | A61B 34/73 600/407 |
| 2003/0011624 | A1* | 1/2003 | Ellis | G16H 10/60 345/646 |
| 2008/0177136 | A1* | 7/2008 | Wang | A61B 1/041 600/109 |
| 2009/0068620 | A1* | 3/2009 | Knobel | A61C 1/082 433/223 |
| 2009/0306509 | A1* | 12/2009 | Pedersen | G01S 15/8936 600/446 |
| 2010/0130853 | A1 | 5/2010 | Chandonnet et al. | |
| 2010/0274389 | A1* | 10/2010 | Ortmaier | A61B 90/36 700/258 |
| 2011/0015521 | A1 | 1/2011 | Faul | |
| 2011/0054293 | A1* | 3/2011 | Markowitz | G01S 5/0263 600/407 |
| 2011/0178394 | A1 | 7/2011 | Fitzpatrick | |
| 2012/0078236 | A1* | 3/2012 | Schoepp | A61B 5/061 606/1 |
| 2012/0157887 | A1* | 6/2012 | Fanson | A61F 2/46 600/595 |
| 2013/0027186 | A1* | 1/2013 | Cinbis | A61B 5/0002 340/10.1 |
| 2013/0066196 | A1* | 3/2013 | Graumann | A61B 6/12 600/424 |
| 2013/0076157 | A1* | 3/2013 | Stein | A61F 2/442 307/116 |
| 2013/0193188 | A1* | 8/2013 | Shelton, IV | A61B 17/068 227/175.2 |
| 2015/0136947 | A1* | 5/2015 | Barak | G01S 17/86 250/206.1 |
| 2015/0206456 | A1* | 7/2015 | Foster | G09B 23/285 434/262 |
| 2016/0209248 | A1 | 7/2016 | Hasler | |

OTHER PUBLICATIONS

International Search Report dated Jul. 20, 2016.
Written Opinion of the International Search Authority dated Jul. 20, 2016.
Arun et al., "Least Square Fitting of Two 3D-Point Sets," IEEE Trans on Pattern Analysis and Machine Intelligence, vol. 9 No. 5, pp. 698-700, 1987.
Grenet et al., "SpaceCoder: a Nanometric 3D Position Sensing Device", CSEM Scientific & Technical Report 2011.
Hartley, R.I. and Sturm, P., "Triangulation." Computer vision and image understanding, vol. 68, No. 2, pp. 146-157, 1997.
Pintaric, T. and Kaufmann, H., Mar. 2007, Affordable infrared-optical pose-tracking for virtual and augmented reality. In Proceedings of Trends and Issues in Tracking for Virtual Environments Workshop, IEEE VR, pp. 44-51.
Wiles, A.D., Thompson, D.G. and Frantz, D.D, "Accuracy assessment and interpretation for optical tracking systems," Proceedings of SPIE, vol. 5367, pp. 421-432, 2004.

* cited by examiner

REDUNDANT RECIPROCAL SURGICAL TRACKING SYSTEM WITH THREE OPTICAL TRACKERS

CROSS REFERENCE TO RELATED APPLICATIONS

The present application is a U.S. national stage application of PCT/IB2016/051242 filed on Mar. 4, 2016 designating the United States, and claims priority to U.S. provisional application Ser. No. 62/128,585 filed on Mar. 5, 2015, the content of these earlier applications being incorporated by reference in their entirety in the present application.

FIELD OF THE INVENTION

The present invention relates generally to redundant reciprocal tracking systems and more specifically it relates to an optical tracking system where at least two trackers are sensing each other in order to compute a rigid transformation based on an over-determined system.

BACKGROUND OF THE INVENTION

Optical tracking systems for tracking the pose (that is the position and orientation) of moving objects in a reference frame or system are known in the literature and prior art. These tracking devices usually use one or several camera sensors. For example, in U.S. Pat. No. 5,227,985 issued to Daniel F. De Menthon, and entitled "Computer vision system for position monitoring in three dimensions using non-coplanar light sources attached to a monitored object" (the content of this patent being incorporated by reference in its entirety in the present application), the tracking system is composed of one camera sensor, and a pose estimation is realized after identifying four or more characteristic non-planar points (further called fiducials or sensed elements). These fiducials placed at known positions are defining a rigid body. In case of a setup of two or more cameras, triangulation is used to find the pose of a rigid body having three or more non-collinear identified fiducials. These fiducials may either be (a) reflective: they reflect light (e.g. reflective spheres or disks), (b) passive: image processing is used to detect specific patterns or (c) active: they transmit light (e.g. visible LEDs, Infrared LEDs, bulbs and more generally light sources). A typical active system is presented in U.S. Pat. No. 4,649,504 issued to Nicholas Krouglicof & al, and entitled "Optical position and orientation measurement techniques", the content of this patent being incorporated by reference in its entirety in the present application.

Redundancy can be integrated in conventional tracking systems by adding more fiducials on objects to track. A rigid registration error (e.g. "Least-Squares Fitting of Two 3-D Point Sets", author Arun & al, 1987 IEEE, the content of this document being incorporated by reference in its entirety in the present application) enables to compute the pose between the theoretical and the measured 3D positions of the fiducials. With such a technique, it is possible to get an error metric related to the quality of the correspondences between the two sets of 3D points. This error give the possibility to provide a rejection threshold on the pose measurement. For example, partial occlusion of the fiducials, irregularities of the reflective material or even dirt or blood on the fiducial can be detected through this technique. The measurement can thus be partly or entirely rejected which is appreciable in application requiring a high level of safety.

A complete characterization of rigid bodies in a stereo camera setup can be found in "Accuracy Assessment and Interpretation for Optical Tracking Systems", chapter 4 and 5, authors Andrew D. Wiles & al, published in SPIE Medical Imaging, Proc. 5367, 2004, the content of this document being incorporated by reference in its entirety in the present application).

Stereo cameras usually comprise two sensors with a known orientation and position, each of them basically being able to detect horizontal and vertical angles. When determining a 3D position of a point in space, the system is over-determined as a minimum of 3 DoF (Degrees of Freedom) are necessary and 4 DoF are actually used to compute the point in space. The fourth DoF is therefore redundant and can be used to evaluate if the system is decalibrated by using either (a) the distance between the centroid of the fiducials in the images and their respective left and right projections of the 3D point, (b) the distance between the 3D lines defined by the fiducials in the images and the optical centers, or (c) the distance of a centroid with respect to the epipolar line related to the centroid in the other image. A complete description of the different error metrics and triangulation techniques can be found either in the computer vision stereo systems literature or in "Triangulation", authors Richard I. Hartley & al, published in Computer Vision and Image Understanding, Vol. 68, No. 2, pp. 146-157, 1997, the content of this document being incorporated by reference in its entirety in the present application.

Other types of optical sensors can be used to determine 3D position of fiducials in space. For example in "spaceCoder: a Nanometric 3D Position Sensing Device", author E. Grenet & al, published in CSEM Scientific & Technical Report 2011 (the content of this document being incorporated by reference in its entirety in the present application), the "spaceCoder" system comprises three parts: (a) a source of illumination face to (b) an image sensor at a given distance, and in-between (c) a transparent scale with a double marking (absolute and regular). The emitted light projects the shadow of the pattern onto the sensor. The high-resolution absolute position of the scale regarding the sensor is obtained combining the coarse absolute position (absolute code) with its fine relative position (regular pattern phase). This principle has been extended to 2-DOF, the pattern on the code-plate being composed of an absolute 2D binary code and a regular 2D pattern. The high robustness, precision and accuracy are essentially due to the fact that the information is distributed over the whole image: each pixel gives its contribution to the fine positioning. Given two 2-DOF spaceCoders placed at a known relative rigid transformation, it is possible to get the 3D position of the light source by means of triangulation. Other arrangement of the scale enable to triangulate directly on a unique 2D sensor and to output the 3D position of the light source. The 3-DOF principle of the spaceCoder technology can easily be extended to 6-DOF. For this, the spaceCoder sensor has to detect the 3D position of at least three independent light sources, which are fixed on the target and define its reference frame. In the present specification, the mention of "spaceCoder" or "spaceCoders" will refer to the "spaceCoder" described in this publication, unless otherwise stated.

Reciprocal optical tracking systems are not commonly found in prior art literature. Such systems requires at least two sensors. Fiducials should be fixed on the sensors' assembly at a known positions. In the frame of the present application, we define a "tracker" as the assembly comprising at least one sensor and at least one fiducial, the position and orientation of all the elements being known. If a system comprises two trackers each of them able to detect 3D fiducials, a total of three fiducials on both trackers is theoretically sufficient to compute the pose between them. The lack of redundancy of such a setup is unfortunately not appropriate in applications requiring a high level of safety.

Computer assisted surgical systems comprising a tracking system must have redundancy in order to reduce the risk of injury or death of the patient undergoing surgery. As existing systems are not reciprocal, they are using a classical optical tracking system combined with at least two rigid bodies. Rigid bodies are most often redundant and comprise four or more fiducials. One rigid body is fixed on the patient, other ones are fastened on surgical equipment and/or surgical instruments. In the workflow of a classical computer assisted surgery operation, it is necessary to put in correspondence the pre-operative dataset of the patient (e.g. MRI, CT series) with the actual patient. This phase is known as rigid registration. To proceed, the surgeon is usually palpating with a pointer three or more anatomical landmarks already identified and marked in the pre-operative dataset. A rigid body is fixed on the patient. The pointer is equipped with another rigid body, where the pointer tip position and direction is known with respect to the frame of reference of the rigid body. After registration, the computer is able to put in relation the reference frame of the pre-operative dataset/planning with the reference frame of the tracking system enabling to guide the surgeon during critical steps of the procedure (e.g. inserting a biopsy needle at the good position, placing an orthopaedic implant at the good position and orientation, etc.). Sometimes, the patient's rigid body has to be removed and/or exchanged. It may occur when (a) reflective spheres (such as markers or fiducials) are dirty or (b) a battery powering active fiducials is low. If the system is not designed to have a reproducible fixation, the rigid registration step should be redone after reinstalling a new rigid body.

Another example using a reproducible fixation can be found in "Apex Robotic Technology: APEX Knee Surgical Navigation with the PRAXIM Robotic Cutting Guide", copyright by OMNIlife science, 2011, Rev 07/11 at page 46: "For easier access, remove the "G" (rigid body) from the NanoBlock using the push-button on the reproducible fixation." In this case the reproducible fixation is used for ergonomic reasons to improve accessibility of the patient.

It is important to point out that not only technical aspects but also safety and workflow constraints should be taken into account when integrating a surgical optical tracking system. As such, reciprocity, redundancy and a reproducible fixation are three key aspects that this invention improves compared to state-of-the art systems.

BRIEF SUMMARY OF THE INVENTION

The invention generally relates to a redundant reciprocal tracking system which includes at least two Trackers and a Central Processor.

There has thus been outlined, rather broadly, some of the features of the invention in order that the detailed description thereof may be better understood, and in order that the present contribution to the art may be better appreciated. There are additional features of the invention that will be described hereinafter.

In this respect, before describing embodiments of the invention in detail, it is to be understood that the invention is not limited in its application to the details of construction or to the arrangements of the components or to the embodiments set forth in the following description or illustrated in the drawings. The invention is capable of other embodiments and of being practiced and carried out in various ways. Also, it is to be understood that the phraseology and terminology employed herein are for the purpose of the description and should not be regarded as limiting. The present invention thus covers additional elements as described, for example means and technical elements equivalent to those described herein, all within the scope of the present invention.

An aim and object of the present invention is to improve the known devices, methods a systems used in tracking applications.

A further object of the present invention is to provide a redundant reciprocal tracking system for simultaneously enabling a first tracker to sense at least a second tracker in the reference frame of the first tracker, the second tracker being able to sense the first tracker in the reference frame of the second one. Both sensing data are transferred to a central processor (typically a computer with appropriate programs and memory capabilities) that will compute the pose (position and orientation) between the reference frames. Even if the minimal requirements are to solve a 6 DoF (Degrees of Freedom) problem—three translations (x,y,z) and three orientations (alpha, beta, gamma)—the overall tracking system is designed to be over-determined. This over-determination is used either to improve the quality of the measure or to evaluate its performances (i.e. pertinence of the measure, decalibration of the system).

Another object of the present invention is to provide a redundant reciprocal tracking system with one or more reproducible fixations that can be used within a computer assisted surgery (CAS) system. The reproducible fixations enabe the replacement of the trackers during the intervention without requiring to recalibrate instruments or to reregister the patient, a clear improvement over known devices and systems.

Another object of the present invention is to provide a redundant reciprocal tracking system that can be used within a computer assisted surgery (CAS) system.

Another object of the present invention is to provide a redundant reciprocal tracking system that can be used within a robotic assisted surgery system.

Another object of the present invention is to provide a redundant reciprocal tracking system that can be used within an intelligent tool assisted surgery system.

Another object of the present invention is to provide a redundant reciprocal tracking system that can be used within a navigated minimal invasive surgery system.

Another object of the present invention is to provide a redundant reciprocal tracking system that can be used within a physical rehabilitation/therapy system.

Another object of the present invention is to provide a redundant reciprocal tracking system that can be used in a motion capture system.

Another object is of the present invention to provide a redundant reciprocal tracking system that can be used in a natural user interface system.

Another object of the present invention is to provide a redundant reciprocal tracking system that can be used for general metrology/spatial measurement applications.

Other objects and advantages of the present invention will become obvious to the reader and it is intended that these objects and advantages are within the scope of the present invention. To the accomplishment of the above and related objects, this invention may be embodied in the form illustrated in the accompanying drawings, attention being called to the fact, however, that the drawings are illustrative only, and that changes may be made in the specific construction illustrated and described within the scope of this application.

In an embodiment, the invention concerns a tracking system and method comprising at least two trackers wherein a first tracker is able to sense positional information of a second tracker in a first reference frame and the second tracker is able to sense positional information of the first tracker in a second reference frame. The positional information of both first and second trackers enables then to calculate the pose of one tracker with respect to the reference frame of the other tracker, the computation being over-determined with more than 6 DoF. The tracking system further comprises means, such as communication means, for the trackers to send their positional information to either a central processor or to a distributed setup of processors that may be integrated in the trackers and means for the processor or setup of processors to combine the positional information of at least two of said trackers and to compute the rigid transformation of one reference frame with respect to the other. In this system the over determination of the mathematical system enables to estimate the quality of this transformation and/or to reduce the measurement noise and/or to improve the quality of the computed transformation.

In an embodiment, the positional information is the pose of the trackers and the tracking system comprises means for the processor(s) to evaluate the pose of one of said trackers with respect to the other of said trackers, to combine these poses in a transformation and/or estimate the quality of this transformation and/or improve the transformation computation by taking into account a reciprocal measure between trackers as redundant data.

In an embodiment of the system, each tracker of said at least two trackers may comprises at least an optical sensing element and three or more light sources that are at known position with respect to the optical sensing element, the optical sensing element of one tracker being able to identify and detect the position in 3D of at least three individual light sources emitted by another tracker. The known position may be a fixed position or a moving position which has for example a known pattern.

In an embodiment of the tracking system the sensing element may be a 3-DoF spaceCoder and the sensed elements may be light sources.

In an embodiment of the tracking system, the optical sensing element may comprise at least two 2-DoF space-Coders, the sensed elements being light sources and the position and orientation between the spaceCoders is known which enable to compute the 3D position of the light sources by means of triangulation. The extra DoF when computing the 3D position may be used to evaluate the decalibration of the Tracker.

In an embodiment of the tracking system, the light sources are preferably emitting in a spectrum not visible by the human eye (e.g. near infrared). Other spectrum (visible) is also possible in the scope of the present invention.

In an embodiment of the tracking system the processing is distributed and done in the trackers which comprise an appropriate processor.

In an embodiment of the tracking system, said trackers comprise a reproducible fixation localized at a known rigid transformation in the reference frame of the tracker such that said trackers may be attached to an object having a part complementary with said reproducible fixation, or released, or reattached or even exchanged while delivering the same pose data to the processor(s).

In an embodiment of the tracking system, said at least one tracker is integrated or fixed on a medical tool and/or on a medical equipment.

In an embodiment of the invention, the tracker is disposable and may be conditioned in a sterile package. It preferably comprises means to turn on the energy of the tracker automatically when required.

In an embodiment of the tracking system, the means to turn on the tracker may be a sensor (e.g. a photo-receptor) which detects a change in the environment to wake-up the electronics when said tracker is taken out from a package, for example the sterile package.

In an embodiment of the tracking system, the mechanism to turn on the tracker may be an electrical contact that is conductive when the tracker is attached to its fixation.

In an embodiment, the tracking system comprises at least three trackers, wherein the first tracker senses the second tracker and vice-versa, the second tracker senses a third tracker and vice-versa, wherein the rigid transformation of the third tracker with respect to first reference frame can be indirectly determined by a combination of transformations including the poses of the second tracker.

In an embodiment, the tracking system may be used in a medical, surgical, radio-interventional or rehabilitation context.

In an embodiment of the tracking system, the redundancy of the system is used to reduce the risk of injury or death of the patient.

In an embodiment, the present invention concerns a tracker as defined herein. Such trackers may be disposable, sterilisable or partly sterilisable.

In an embodiment the invention, it relates to an apparatus using a tracking system and trackers as described and detailed herein.

The apparatus may be a medical, surgical, radio-interventional or rehabilitation apparatus.

The present invention also relates to a tracking method using the tracking system or trackers as described and detailed herein.

The tracking method may be used in a medical, a surgical, a radio-interventional or a rehabilitation application, for example.

The method according to the present invention is defined in the appended independent claims and the dependent appended method claims define further embodiments of the method according to the present invention.

BRIEF DESCRIPTION OF THE DRAWINGS

Various other objects, features and attendant advantages of the present invention will become fully appreciated as the same becomes better understood when considered in conjunction with the accompanying drawings, in which like reference characters designate the same or similar parts throughout the several views, and wherein.

DETAILED DESCRIPTION OF THE INVENTION

Figure 1:
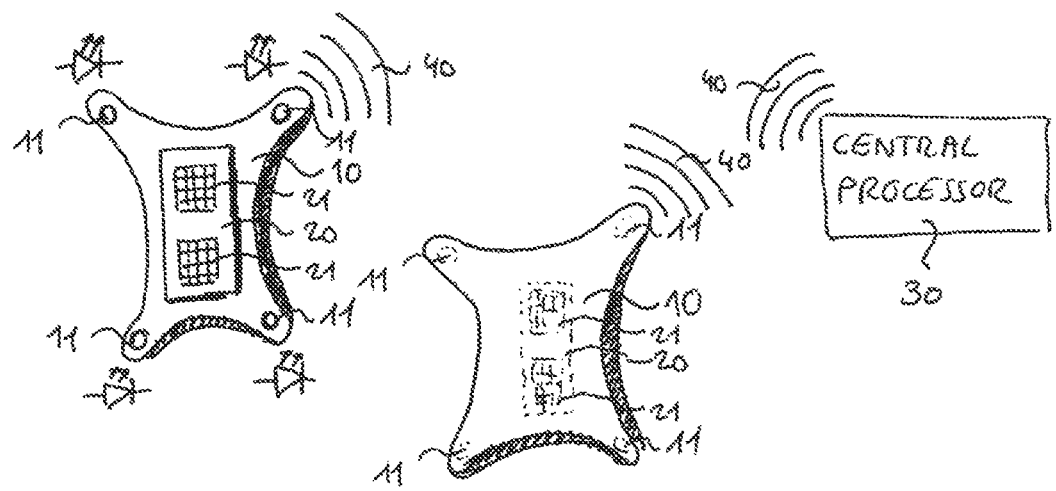
FIG. 1 is a perspective view of an embodiment of the present invention.

FIG. 1 presents as an embodiment of the invention an optical variation of a Redundant Reciprocal Tracking System, which is comprises two Trackers 10. They are facing each other in the figure. Four Light Sources—or Sensed Elements 11—are rigidly fixed to each Trackers. Each Trackers comprises a sensor sub-assembly 20 fixed with respect to the Light Source(s). The Sensor sub-assembly comprises two 2D Optical Sensor Modules 21. This Sensor sub-assembly is able to detect the 3D positions (with 4 DoF) of the distinct Light Sources located on the other Tracker via triangulation of the two Optical Sensors Modules. The over-determination of the 3D measure enabling to get information either on Tracker decalibration or measurement problem. If three or more Light Sources present on the other Tracker are detected, it is also possible to calculate the pose (position+orientation) of the other Tracker. The other Tracker can symmetrically or reciprocally perform the same type of measurement by mean of its own Sensor sub-assembly. Data of one and/or two Trackers are further transferred to the Central Processor 30 via a wired or wireless Link 40. Note that this Central Processor could alternatively be part of a Tracker. The reciprocal pose measure can be used.

Figure 2:
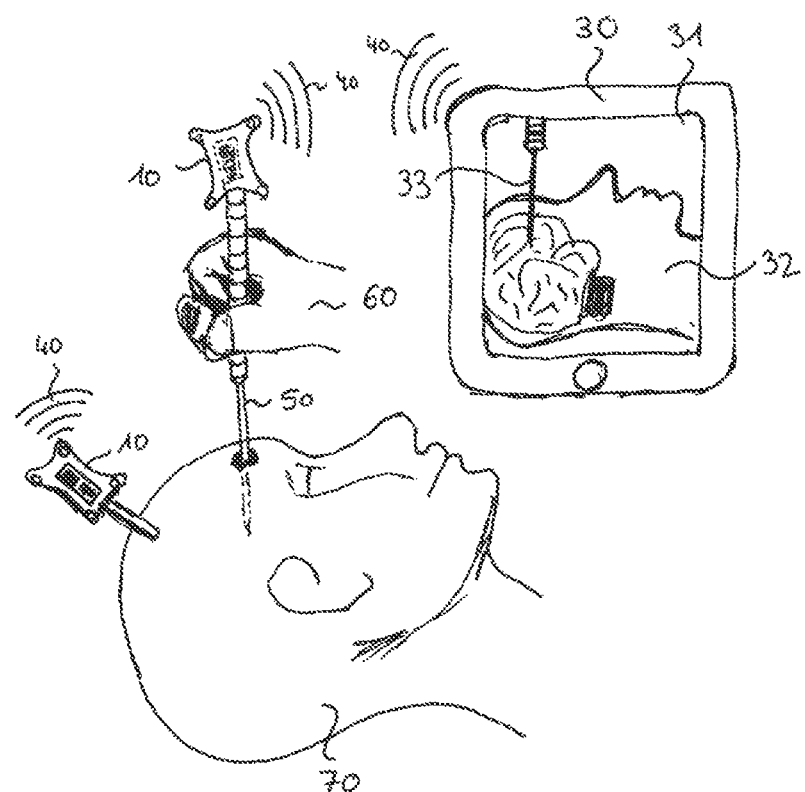
FIG. 2 is a perspective view of another embodiment of the present invention.

FIG. 2 presents as an embodiment of the present invention: an optical version of the proposed Redundant Reciprocal Tracking System in a Computer-Assisted Surgery (CAS) setup. One Tracker 10 is rigidly fixed on the skull of the patient. The other is located on a Biopsy Needle 50 and operated by a Surgeon/Radiologist 60. The setup further comprises a Tablet 30 and a Touch Screen 31. Both Trackers are continuously sending their respective pose via a wireless Link 40. After a registration of the preoperative images (CT, MRI, etc.) with respect to the patient and the calibration of the biopsy needle—the pose of the Tracker with respect to needle's tip and axis should be known—, it is possible to display the position and trajectory of the needle 33 within the pre-operative images and/or within a corresponding 3D representation 32.

Figure 3:
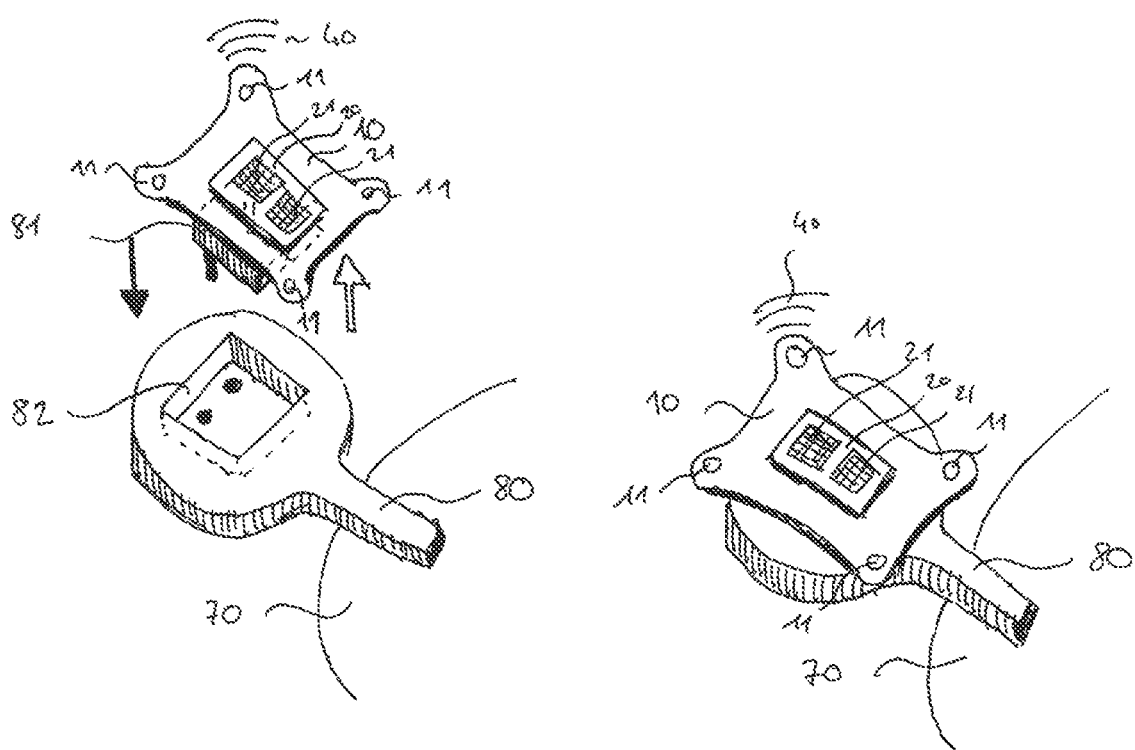
FIG. 3 is a perspective view of another embodiment of the present invention.

FIG. 3 illustrates a similar setup as the one of FIG. 2. This configuration further comprises a reproducible fixation 81 on the Tracker 10 located on the Patient. The reproducible fixation counterpart 82 is integrated in the mechanical structure which is rigidly fixed on the Patient 70. The reproducible fixation is designed such that both parts can be clipped and released. When clipped, the fixation should be as tight as possible. Left drawing illustrates when the Tracker is detached from the reproducible fixation, right drawing when it is attached. The reference frame of a Tracker having a reproducible fixation is defined with respect to the fixation itself in order for the Tracker to be exchanged without requiring a re-registration or re-calibration. The reproducible fixation can use any means to reach this aim: corresponding shapes (as illustrated as an example in FIG. 3), markings, couplings, etc.

Figure 4:
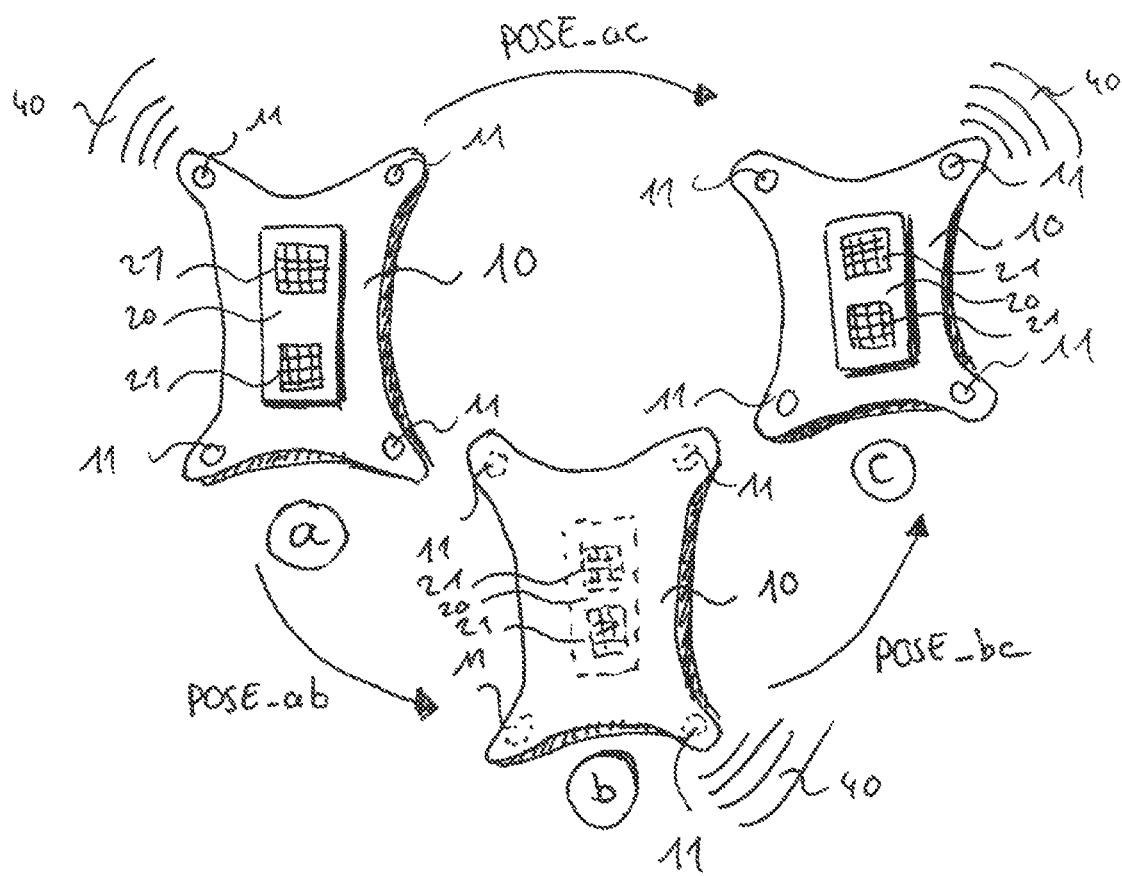
FIG. 4 is a perspective view of another embodiment of the present invention.

FIG. 4 illustrates an alternative embodiment of the present invention. It shows a configuration with three Trackers 10 named (a), (b) and (c). Trackers (a) and (b) are ideally not seeing each other, Tracker (b) is facing both Trackers (a) and (c) and is able to sense them. Trackers (a) and (b) are able to sense each other and to compute a pose (POSE_ab). Trackers (b) and (c) are able to sense each other and to compute a pose (POSE_bc). Pose between Trackers (a) and (c) (POSE_ac) is a combination of POSE_ac and POSE_bc.

Figure 5:
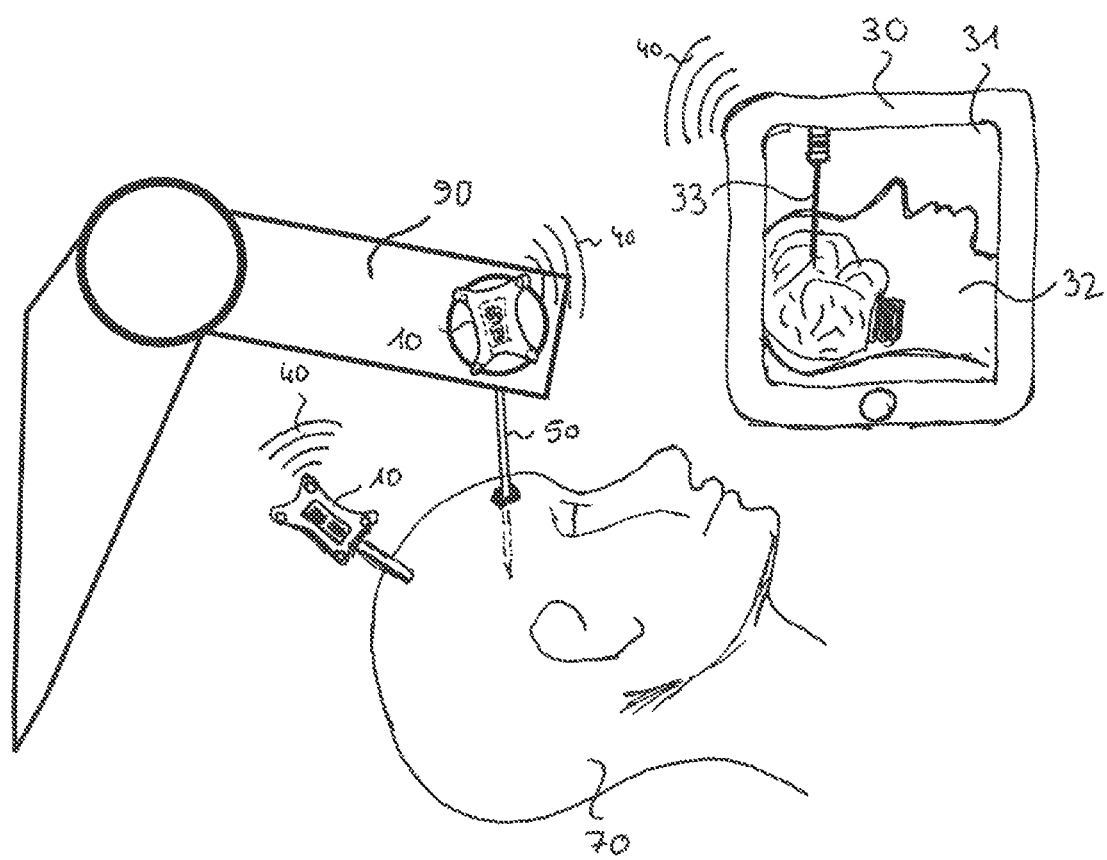
FIG. 5 is a perspective view of another embodiment of the present invention.

FIG. 5 presents as an embodiment of the present invention: an optical version of the proposed Redundant Reciprocal Tracking System in a Robotic-Assisted Surgery setup. One Tracker 10 is rigidly fixed on the skull of the patient. The other is located on the Robot 90 or robot arm, the Biopsy Needle 50 being at a known position with respect to the end-effector of the robot. Alternatively, the Robot 50 can just replace the human 60 of FIG. 2 and directly hold the biopsy needle 50. The setup further comprises a Tablet 30 and a Touch Screen 31. Both Trackers are continuously sending their respective pose via a wireless Link 40. In this embodiment, the tracker 10 on the robot could alternatively send poses or positional information through a wired link integrated in the robotic structure. After a registration of the preoperative images (CT, MRI, etc.) with respect to the patient and the calibration of the biopsy needle—the pose of the Tracker with respect to needle's tip and axis should be known—, it is possible to display the position and trajectory of the needle 33 within the pre-operative images and/or within a corresponding 3D representation 32.

Figure 6:
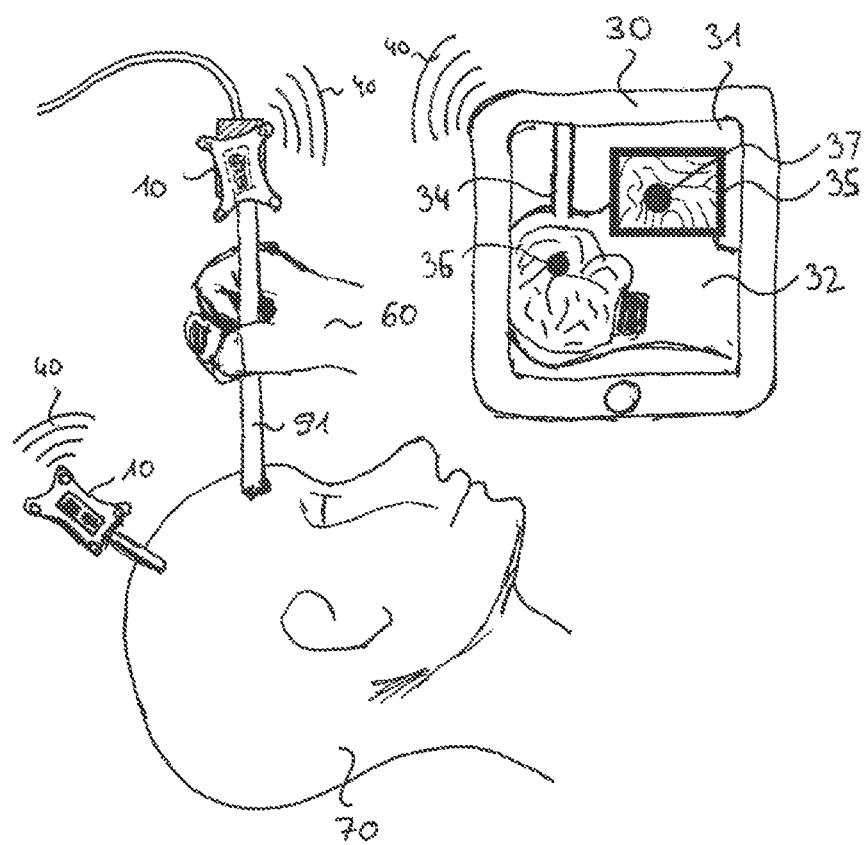
FIG. 6 is a perspective view of another embodiment of the present invention.

FIG. 6 presents as an embodiment of the present invention: an optical version of the proposed Redundant Reciprocal Tracking System in an endoscopic setup. One Tracker 10 is rigidly fixed on the skull of the patient 70. The other is located on the endoscope 91 and operated by a Surgeon 60. The orientation and position of the endoscope tip with respect to the tracker is known. Alternatively, the intrinsic parameters (focal distances, optical centre) of the endoscopic camera are known in order to provide a more precise augmented reality 37. Ideally, the tracker on the endoscope is fixed with a reproducible fixation (not shown here). The setup further comprises a Tablet 30 and a Touch Screen 31. Both Trackers 10 are continuously sending their respective pose via a wireless Link 40. In this case, the tracker on the endoscope 91 could send poses through a wired link integrated in the endoscope. After a registration of the preoperative images (CT, MRI, etc.) with respect to the patient 70 and the calibration of the endoscope 91, it is possible to display the position and trajectory of the endoscope 34 within the pre-operative images and/or within a corresponding 3D representation 32. An overlay of the endoscopic image is visible in the application. If trajectories and/or anatomical landmarks 36 (e.g. a tumour) are segmented (and/or specified) in the preoperative data, it is possible to display them in the endoscopic image 37 providing augmented reality to the surgeon.

Figure 7:
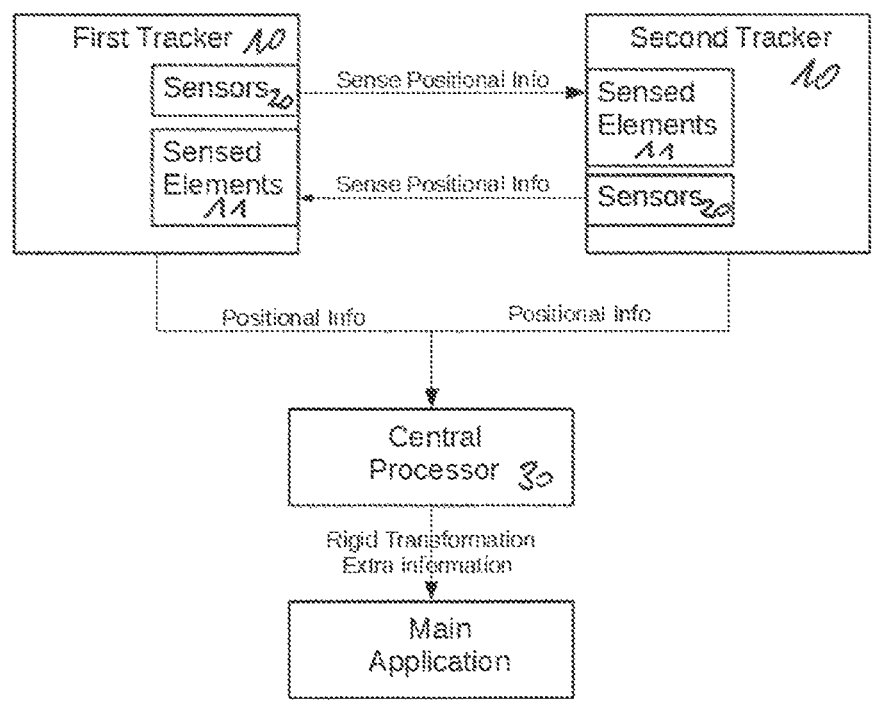
FIG. 7 is a block-diagram of an embodiment of the present invention.

FIG. 7 illustrates a block diagram of an embodiment of the method according to the present invention with arrows showing the exchange of information between the elements of the system as described herein in reference to the several embodiments of the present invention. The trackers sense positional information (for example pose) and this information is used in the main application as described in detail in the present application, for example of a device using the tracking system of the present invention.

A. Overview

Turning now descriptively to the drawings, in which similar reference characters denote similar elements throughout the several views, the figures illustrate at least two Trackers—both comprising at least one Sensor and Sensed Elements—and a Central Processor. The following description will discuss in more detailed manner the elements and features of the present invention by reference to the drawings.

B. Tracker

A Tracker 10 comprises at least one Sensor 20 and one or more Sensed Elements 11. Trackers 10 are intended and designed to be fixed on the objects to be tracked (e.g. surgical tools, surgical equipment, patient, etc.). Sensed Elements 11 and the Sensor(s) 20 are disposed at known position and orientation with respect to the frame of reference of the Tracker 10. The positioning of the elements can either be achieved by a precise manufacturing or by using an individual calibration method. Trackers 10 are facing each other in a way that Sensor(s) 20 from a first Tracker 10 can sense one or several Sensed Elements 11 located on another Tracker 10 and vice-versa. The Sensor(s) 20 are able to get positional information of the Sensed Elements 11 with a number of DoF (Degrees of Freedom) that depends on the Sensor 20 type. In a theoretical system, a minimum of 6 DoF is required to compute both the position and orientation of a first Tracker 10 with respect to a second Tracker 10. In a configuration where the Sensor 20 is able to get the 3D position of a fiducial, a total of three fiducials placed on both Trackers 10 define this minimum requirement. Having more than 6 DoF is mandatory in several applications like surgical ones in order to provide a higher safety as for example has been described above. This is achieved by either adding redundancy in the Sensors 20 and/or in the Sensed Elements 11. Redundancy enables to improve the quality of the measurements by mean of statistical methods. The system will moreover be more tolerant to noise as the influence of outliers will be diminished. Redundancy can also provide an error metric related to (a) the status of the Trackers 10 (e.g. is a Tracker decalibrated) and/or (b) the status of the measurements (e.g. is a Sensed element 11 dirty, partly occluded, etc.). This error metric can further used by the application to decide if the measurements made are reliable or not.

Typical Sensor 20 and Sensed Elements 11 could be optical ones. In this case, the Sensed Elements 11 could be Light Sources (preferably near Infrared LEDs). In the optical configuration, the Sensor 20 may be an array of optical detectors in a combination that allows retrieving the distinct 3D positions of the photons generated by the Light Sources. A typical optical tracker would have an electronic circuitry comprising at least the sensor(s), a CPU, persistent memory, a communication link (e.g. wired cable, Bluetooth, WiFi, LiFi, or other equivalent communication technology etc.) and a power source (e.g. battery or an accumulator, rechargeable battery). At least the Sensor 20 and the Sensed Elements 11 should be manufactured in a rigid housing or in a mobile configuration where their relative position and orientation is fixed and perfectly known during the acquisition. In a rigid housing, their exact position and orientation can be either determined once if the manufacturing is very precise or individually calibrated. Calibration as well as other information like the tool tip, the tool axis, etc. may be stored in a persistent memory (for example in a chip or other similar electronic element) in the Tracker 10 and sent to the Central Processor 30 for further pose processing of the different Trackers 10 used in the system.

A Reproducible Fixation 81 can be part or attached to the Tracker 10. The Reproducible Fixation 81 is at a known and invariable position and orientation with respect to the frame of reference of the Tracker 10. The Reproducible Fixation 81 attaches to the object to be tracked via a complementary part 82. The Tracker 10 is thus preferably designed such that if released, reattached or even exchanged with a different or new Tracker 10, the same measurement will be provided. The position of the tracker is thus unique and non-variable. This can be for example achieved by defining the frame of reference of all the Tracker 10 on the Reproductible Fixation 81. Accordingly, a Tracker may be exchanged at any time without loss of the calibration.

The link between the Trackers 10 could be wired or wireless (e.g. Bluetooth, Zigbee, WiFi, LiFi, Optical Communication, IrDA, etc.). Extra information such as tracker id, serial numbers, calibration, temperature, button status and other sensor and meta-data can be exchanged through this link.

C. Sensor(s)

In the present application, the term Sensor(s) 20 refers to either a single Sensor or a subsystem comprising several Sensors where their respective orientation and position is known during the measure. They are preferably fixed but could also move.

A Sensor 20 is fixed on the Tracker 10 at a known orientation and position with respect to its frame of reference. The role of the Sensor 20 is to get positional information of the Sensed Elements 11 visible within the field of view (the notion of "visible" and "view" are used herein in their abstract definition, so that in a real application, a non-optical sensor could also be used if it has an equivalent effect) of the Sensor 20 and located on another Tracker 10. The distinct positions of the detected Sensed Elements 11 of a set of two Trackers 10 are further used in the Central Processor 30 to determine at least the 6 DoF required to compute the rigid transformation between them.

Typical Sensor 20 and Sensed Elements 11 could be optical ones. In this case, the Sensed Elements 11 could be Light Sources (preferably near Infrared LEDs).

An optical sensor could comprise one or more 1D optical sensor modules 21. In this case, the light detected by an optical sensor module 21 defines a single angular information (1 DoF). A Sensor 20 comprising three 1D optical sensor modules 21 oriented in at least two different directions provides the 3D position of a light source by mean of triangulation. In this setup, three light sources 11 are sufficient to compute a 6 DoF pose. An example of 1D optical sensor could be: (a) a camera linear sensor (e.g. CCD/CMOS), (b) a Position Sensitive Detector (PSD), (c) an optical system comprising either a combination of diaphragm with a cylindrical lens, (d) a mask pattern positioned in front of the camera sensor (e.g. 1 DoF spaceCoder as described herein).

Another type of optical sensor could comprise one or more 2D optical sensor modules 21. In this case, the light detected by an optical sensor module defines two angular information (2 DoF). A Sensor comprising two 2D optical sensor modules provides the 3D position of a light source (by mean of triangulation) with 4 DoF. The extra DoF enables to detect the decalibration of the system using (a) the reprojection error, (b) distance to the epipolar lines or (c) 3D distance of lines defined by optical centers and the center of the fiducial in the image. These error metrics are described in the background section of the present application (see above). Examples of 2D optical sensor could be: (a) a CMOS/CCD camera array sensor with diaphragm and lens(es) (e.g. a conventional digital camera system) or (b) simply a mask pattern placed in front of the camera sensor (e.g. 2 DoF SpaceCoder as described herein).

An alternate solution for a 2D optical sensor module 21 is to use a Dynamic Vision Sensor (DVS) instead of a CMOS/CCD. The main difference between a DVS and a normal CMOS camera is that the DVS output is a stream of events that encode changes in the brightness. Each event encodes the location of the change, whether there was a positive or negative change in brightness. A DVS has the advantage of enabling the Light Sources to simultaneously send data while being tracked. In this configuration, the Light Sources can all be turned on (without any sequential limitation) while sending identification data.

Another type of optical sensor could comprise one 3D optical sensor module 21. A possible module could comprise (a) a CMOS/CCD array sensor, including an optical system enabling to perform triangulation on a single array sensor (e.g. 3 Dof spaceCoder as described herein) from CSEM, (b) a time of light based camera.

Any combination of 1D, 2D and 3D optical sensor modules is of course possible within the scope of the present invention.

Near infrared filter pass band filter may be used in combination with infrared LEDs to improve the robustness of a solution based on optical sensors.

Other Sensors technologies are possible using other technologies like ultrasound, magnetism, or even light-field, etc.

In case of light-field sensor, sensor enable to sense both light sources position and coming ray orientation. With this extra information (position and angles), triangulation and identification of fiducials is more efficient (time, quality, etc.).

D. Central Processor

The Central Processor 30 is gathering (raw, pre-processed, and/or processed) data from the different Sensors 20 located on the Trackers 10 via a wired or wireless Link 40. The Central Processor 30 is further calculating the respective position and orientation of the Trackers based on the gathered data. Triangulation can for example be used to get the 3D position of the Sensed Elements 11. A pose estimation algorithm (see Arun publication in the background section above) can be used to calculate the orientation and position of one Tracker 10 with respect to another Tracker 10. Quality improvement of the measure as well as error metrics can be computed from the over-determined system. Both pose, error metrics and the necessary high-level tracking information are further transferred to the application for appropriate treatment.

The system can furthermore process and/or reprocess positional data using other sensed or external parameters. Such parameters enable to define trustfulness of the measure provided by a given tracker. The measure could be pondered given its trustfulness (in real-time or during post-processing). Trustfulness could be based on the circular (resp. ellipsoid) estimation of spherical (res. Disk) fiducial, a bump sensor detecting shock that could have deformed the tracker, the use of the tracker outside of the optimal usage temperature, etc.

Note that the Central Processor 30 may be integrated within a Tracker 10. The concept may de decentralized if several Central Processors 30 are alternatively present in the system. At minimum, Central Processors 30 should be able to gather data from two distinct Trackers 10 and send the result to the application. A Central Processor 30 may be included in every Tracker 10. Their respective data and/or calculations may be exchanged and the result directly transferred to the main application. In this case, all the metrological processing may be performed in the Trackers 10.

In this invention, the notion of acquiring positional information of reciprocal trackers at the "same time" is related to the sensor technology, the communication protocol and the final application. Ideally, it is simultaneous. Practically if the lag is very small, it could be neglected for the reciprocal measurement. If the lag is longer it should be compensated in the reciprocal measurement (e.g. by extrapolation of interpolation of positional information at the same timestamp).

In case the Sensed Elements 11 are acquired successively, the direct computation of the pose of a moving Tracker 10 is noisy because the acquisition of the entire Sensed Elements 11 is not done at the same time. Noise can drastically be reduced by interpolation or extrapolation of the position of the Sensed Elements 11 at a common timestamp.

The Central Processor 30 may be an electronic board with a processor, an embedded processor (SoC), a PC, a tablet, a Smartphone or directly integrated in the Tracker or any other equivalent equipment. For a tablet application, the Link is preferably Bluetooth or WiFi as non-limiting embodiments.

The Link from the Trackers 10 to the Central Processor 30 may be wired or wireless (e.g. Bluetooth, Zigbee, WiFi, LiFi, via GSM, etc.). In case the Central Processor is directly in the Tracker a bus, i2c, or serial interface may be used).

E. Connections of Main Elements and Sub-Elements of the Invention

Sensed Elements 11 are emitting in a way they are not interfering each other or with the Sensors 20. The system is designed such as the Sensed Elements 11 can be uniquely identified. This identification depends on the sensor technology. In a basic setup, the Sensed Elements are activated the one after the others to guarantee a unique identification. If the activation is simultaneous, one example to solve this problem is described in "Affordable Infrared-Optical Pose-Tracking for Virtual and Augmented Reality", authors T. Pintaric & al, Proceedings of IEEE VR Workshop on Trends and Issues in Tracking for Virtual Environments, March 2007, the content of this document being incorporated by reference in its entirety in the present application. Depending on the Sensor technology used, emissions of the Sensed Elements may be simultaneous, sequential or random. The emission by the Sensed Elements 11 and the reception by the Sensors 20, —both located on the different Trackers 10, —may also be locally or globally synchronized or random. Identification of the Sensed Elements 11 is either implicit or explicit. In an explicit mode, the Sensor Element 20—, or an alternate communication means, —could generate an extra signal to identify itself. In case of Optical Sensor Modules 21, the identification of the emitting LEDs may be done by superposing a hi-frequency signal encoding its id between the acquisition phases of the Sensors 20. At the end, the positional information of the different Sensed Elements 11 visible by the Sensors 20 are captured and identified. Partial or complete spatial 3D position can be computed on the Trackers 10 or later on in the Central Processor 30. Data are transmitted via a Link 40 to the Central Processor 30. The Central Processor 30 aggregates the data. For example, if at least a total of three Sensed Elements 11 are visible by two 3 DoF Trackers 10, it is possible to compute the pose of the Trackers 10. If each Sensor 20 detects three or more Sensed Elements 11 of another Tracker 10, it is possible to compute the pose of first Tracker 10 in the frame of reference of the second Tracker 10 and vice-versa. One pose is theoretically the inverse of the other. This redundancy can be used in a medical application to reduce the measurement risks. Finally, the Central Processor 30 provides the necessary high-level tracking information to the main application 31.

In a setup composed of three Trackers 10 (a, b and c) as presented in FIG. 4, if Tracker a sense Tracker b (and vice-versa) and Tracker b sense Tracker c (and vice-versa), it is moreover possible to compute the pose of Tracker a in the frame of reference of Tracker c (POSE_ac) and vice-versa (POSE_ca). This will be a combination of POSE_ab and POSE_bc. This technique can be extended to any number of Trackers 10 interacting together and determine their relative poses. Such a system allows to handle a complete occultation between two trackers.

In a setup composed of three Trackers 10 (a, b and c), if Tracker a sense Tracker b (but b might not sense a) and Tracker b sense Tracker c (but c might not sense b) and Tracker c sense Tracker a (but a might not sense c), it is moreover possible to provide pose between all trackers with redundancy.

F. Alternative Embodiments of Invention

In an embodiment of the invention, the Sensor(s) 20 of a Tracker 10 comprise at least two 2 DoF spaceCoders as described herein. A 2 DoF spaceCoders is an Optical Sensor Module comprising a camera sensor and a reticule in front of it. The reticule is designed such that when a light source is in front of the sensor, it casts a shadow on the camera sensor through the reticule so that horizontal and vertical angular position of the light source can be retrieved. The SpaceCoders (as described above) are both placed at a known position and orientation on the reference frame of the Tracker 10. In an embodiment of this invention, this baseline is less than 40 mm, reasonably less than 30 mm, ideally less than 20 mm and optimally, less than 10 mm. The other geometrical parameters of the Optical Sensor Modules are well known, so that the 4 DoF position of a light source 11 located on another Tracker 10 can be computed by mean of triangulation. Light sources 11 are emitting sequentially. Identification of the sources 11 and synchronization of the acquisition is realized with a higher speed optical communication that is not interfering with the acquisition of the SpaceCoders. Angular position and/or 3D positions of the LEDs (light sources 11) are further transmitted to the Central Processor 30 via a wireless Link (e.g. Low Power Bluetooth). Pose calculation and optionally cross validation is done on the Central Processor 30. The extra DoF when extracting the position of a LED 11 enable to estimate the decalibration of the Tracker 10 and/or the quality of the measurement. In an embodiment of the invention, at least three LEDs 11 are located on each Tracker 10 allowing to compute the complete pose of a Tracker 10 and its reciprocal. Having both poses enables to easily and rapidly check the quality of the measurement.

In an embodiment of the invention, the Sensor 20 is composed of at least one 3 DoF spaceCoder. A 3 DoF spaceCoder is an Optical Sensor Modules composed of a camera sensor and a reticule in front of it (see the above reference to the prior art publication to Grenet & al of CSEM). The reticule is designed such that when a light source is in front of the sensor, it casts two distinct shadows on the camera sensor. Instead of doing triangulation on two 2 DoF spaceCoders, triangulation is done on two distinct areas of the camera sensor where the shadow is cast. Other elements of this embodiment and processes are similar to the previous embodiment.

In an embodiment of the invention, the proposed Tracking System is installed in a computer-assisted surgery setup (see for example FIG. 2). One Tracker 10 is rigidly fixed on the skull of a patient 70. The other is located on a medical device 50 (for example a Biopsy Needle) and operated by a Surgeon/Radiologist 60. The setup further comprises a Tablet 30 and a Touch Screen 31. Both Trackers 10 are continuously sending their respective poses to a Central Processor (Tablet 30) via a wireless Link 40. After the correct registration of the preoperative images (e.g. CT, MRI, PET) with respect to the patient 70 and the calibration of the axis and tip of the biopsy needle 50, it is possible to display the position and trajectory of the needle 33 within the preoperative images or 3D data 32. Compared to existing surgical systems, this system offers a redundancy of the measure, less occlusion problems, improved ergonomics as well as a better overall accuracy.

The redundancy of the system is also mandatory (a) to reduce noise and (b) to avoid wrong measurements that could cause either injuries or to sample tissues at inappropriate positions.

In an embodiment of the invention, the Tracker 10 located on the patient 70 of the computer-assisted surgery embodiment is equipped with a Reproducible Fixation 81, 82. Removing and replacing the Tracker 10—for example if its battery is too low—after the registration process can easily be done and will not require to re-register the patient in the system.

In an embodiment of the invention, the Tracker 10 located on the Biopsy Needle of the computer-assisted surgery embodiment as well as the Biopsy Needle 50 (or any other instrument used according to the principles of the present invention) are disposable elements. They may be connected together in the sterile package. Needle tip and axis can coincide to the reference frame of the Tracker 10 so that a calibration of the Biopsy Needle 50 is not necessary. The biopsy needle tip and orientation can alternatively be stored in the memory of the Tracker 10.

In an embodiment of the invention, the proposed Tracking System is integrated in a computer/robotic assisted surgery setup (FIG. 5). In this configuration, one or several Trackers 10 are located on the robot's end-effector and at least another Tracker 10 is fixed on the patient 70.

In an embodiment of the invention, the proposed Tracking System is integrated in a minimal invasive surgery (and/or microscope) setup (FIG. 6). In this configuration, one or several Trackers 10 are located on the endoscope/microscope and at least another Tracker 10 is fixed on the patient 70. Tracking information is further used to display information in the endoscope/microscope image like pre-operative planning, position of tumor, points of interest or other tracked instruments 50.

In an embodiment of the invention, the proposed Tracking System is integrated in a physical rehabilitation/therapy system, in a sport's training/learning system, or in any motion capture system. In this configuration, one or more Trackers 10 are fixed on the subject to track/analyze. Other Trackers 10 can be integrated in other parts of the subject, in the room, either on a removable frame, or on a tripod or is following the person on a trolley (e.g. mobile robot, drone). The application records the location of the subject as well as his/her joints movements. These data are further analyzed in a dedicated motion capture application.

In an embodiment of the invention, disposable Trackers can be conditioned in a sterile package. The battery can be pre-installed during the manufacturing stage and electronics is operating in a deep sleep mode. Once the sterile recipient is opened—during the intervention, —a sensor (e.g. a photo-receptor) detects a change in the environment and wake-up the electronics. It allows the system to conditioned the battery inside the Tracker and avoid using an extra power switch.

In an embodiment of the invention, the disposable Trackers can be conditioned in a sterile package. The battery can be pre-installed during the manufacturing stage and electronics is off. Once the Tracker if attached to the Reproducible Fixation, a (conductive) contact or reed switch or is established between the battery and the electronic circuitry enabling to power it up. It allows to avoid using an extra power switch.

What has been described and illustrated herein is a preferred embodiment of the invention along with some of its variations. Also, embodiments and features of different may be combined together according to circumstances and needs and they are not exclusive. The terms, descriptions and figures used herein are set forth by way of illustration only and are not meant as limitations. Those skilled in the art will recognize that many variations are possible within the spirit and scope of the invention in which all terms are meant in their broadest, reasonable sense unless otherwise indicated. Any headings utilized within the description are for convenience only and have no legal or limiting effect.

The invention claimed is:

1. A tracking system comprising memory comprising instructions stored thereon and one or more processors coupled to the memory and configured to execute the stored instructions to:
   obtain from a first tracker first positional information of a second tracker in a first reference frame of the first tracker, from the second tracker second positional information of the first tracker in a second reference frame of the second tracker and third positional information of a third tracker in the second reference frame, and from the third tracker fourth positional information of the second tracker in a third reference frame of the third tracker;
   determine, based on the first, second, third, and fourth positional information, a first pose of the first tracker with respect to the second reference frame and a second pose of the second tracker with respect to the third reference frame;
   determine, based on a combination of transformations including the first pose of the first tracker with respect to the second reference frame of the second tracker and the second pose of the second tracker with respect to the third reference frame of the third tracker, a rigid transformation of the first reference frame of the first tracker relative to the third reference frame of the third tracker;
   output an error metric generated based on an additional degree of freedom above a minimum degrees of freedom required to determine a three-dimensional position, wherein the error metric comprises an indication of a quality of the rigid transformation and each of the first, second, and third trackers comprises at least two two-dimensional optical sensors collectively configured to detect the three-dimensional position with the additional degree of freedom; and
   output, to a display device, within one or more registered images of a patient to which one or more of the first, second, or third trackers is fixed, and based on the rigid transformation, an indication of one or more of a position or a trajectory of a surgical instrument to which another one or more of the first, second, or third trackers is fixed.

2. The tracking system according to claim 1, wherein each of the first, second, and third trackers comprises four or more light sources that have known positions with respect to the optical sensors.

3. The tracking system according to claim 1, wherein each of the first, second, and third trackers comprises a reproducible fixation arranged at a known rigid transformation in one of the reference frames and is configured to be attached, released, reattached, or exchanged with an object having a complementary part with the reproducible fixation.

4. The tracking system according to claim 1, wherein the first, second, and third positional information are acquired at a time difference and the processors are further configured to execute the stored instructions to update the first, second, or third positional information to correspond to a same timestamp before determining the first pose and the second pose.

5. The tracking system according to claim 1, wherein the surgical instrument comprises one or more of a robotic arm, an end-effector of the robotic arm, or an object attached to one or more of the robotic arm or the end-effector of the robotic arm.

6. A method, comprising:
   obtaining from a first tracker first positional information of a second tracker in a first reference frame of the first tracker, from the second tracker second positional information of the first tracker in a second reference frame of the second tracker and third positional information of a third tracker in the second reference frame, and from the third tracker fourth positional information of the second tracker in a third reference frame of the third tracker, wherein each of the first, second, and third trackers comprises at least two two-dimensional optical sensors;
   determining, based on the first, second, third, and fourth positional information, a first pose of the first tracker with respect to the second reference frame and a second pose of the second tracker with respect to the third reference frame, wherein the first and second poses are overdetermined with more than six degrees of freedom as a result of the redundant at least two two-dimensional optical sensors;
   determining, based on a combination of transformations including the first pose of the first tracker with respect to the second reference frame of the second tracker and the second pose of the second tracker with respect to the third reference frame of the third tracker, a rigid transformation of the first reference frame of the first tracker relative to the third reference frame of the third tracker;
   outputting an error metric generated based on an additional degree of freedom above a minimum degrees of freedom required to determine a three-dimensional position, wherein the error metric comprises an indication of a quality of the rigid transformation and the at least two two-dimensional optical sensors are collectively configured to detect the three-dimensional position with the additional degree of freedom; and
   outputting, to a display device, within one or more registered images of a patient to which one or more of the first, second, or third trackers is fixed, and based on the rigid transformation, an indication of one or more of a position or a trajectory of a surgical instrument to which another one or more of the first, second, or third trackers is fixed.

7. The method according to claim 6, wherein each of the first, second, and third trackers comprises four or more light sources that have known positions with respect to the optical sensors.

8. The method according to claim 6, wherein each of the first, second, and third trackers comprises a reproducible fixation arranged at a known rigid transformation in one of the reference frames and is configured to be attached, released, reattached, or exchanged with an object having a complementary part with the reproducible fixation.

9. The method according to claim 6, wherein the first, second, and third positional information are acquired at a time difference and the method further comprises updating the first, second, or third positional information to correspond to a same timestamp before determining the first pose and the second pose.

10. The method according to claim 6, wherein the surgical instrument comprises one or more of a robotic arm, an end-effector of the robotic arm, or an object attached to one or more of the robotic arm or the end-effector of the robotic arm.

11. A non-transitory computer readable medium having stored thereon instructions comprising executable code that, when executed by one or more processors, causes the processors to:

obtain from a first tracker first positional information of a second tracker in a first reference frame of the first tracker, from the second tracker second positional information of the first tracker in a second reference frame of the second tracker and third positional information of a third tracker in the second reference frame, and from the third tracker fourth positional information of the second tracker in a third reference frame of the third tracker, wherein each of the first, second, and third trackers comprises at least three light sources and at least two two-dimensional optical sensors spaced at a known position with respect to each other and the at least three light sources;

determine, based on the first, second, third, and fourth positional information and the known position of the at least two two-dimensional optical sensors, a first pose of the first tracker with respect to the second reference frame of the second tracker and a second pose of the second tracker with respect to the third reference frame of the third tracker, wherein the third reference frame is different than the first reference frame and the first and second poses comprise a three-dimensional position of the at least three light sources of the first and second trackers, respectively, and are overdetermined with more than six degrees of freedom as a result of the redundant at least two two-dimensional optical sensors;

determine, based on a combination of transformations including the first pose of the first tracker with respect to the second reference frame of the second tracker and the second pose of the second tracker with respect to the third reference frame of the third tracker, a rigid transformation of the first reference frame of the first tracker relative to the third reference frame of the third tracker;

output an error metric generated based on an additional degree of freedom above a minimum degrees of freedom required to determine a three-dimensional position of the at least three light sources using the two two-dimensional optical sensors, wherein the error metric comprises an indication of a quality of the rigid transformation and the first tracker is not visible to the third tracker, and vice-versa, at a time at which the first, second, third, and fourth positional information is obtained; and output, to a display device, within one or more registered images of a patient to which one or more of the first, second, or third trackers is fixed, and based on the rigid transformation, an indication of one or more of a position or a trajectory of a surgical instrument to which another one or more of the first, second, or third trackers is fixed.

12. The non-transitory computer readable medium of claim 11, wherein each of the first, second, and third trackers comprises four or more light sources that have known positions with respect to the optical sensors.

13. The non-transitory computer readable medium of claim 11, wherein each of the first, second, and third trackers comprises a reproducible fixation arranged at a known rigid transformation in one of the reference frames and is configured to be attached, released, reattached, or exchanged with an object having a complementary part with the reproducible fixation.

14. The non-transitory computer readable medium of claim 11, wherein the first, second, and third positional information are acquired at a time difference and the executable code, when executed by the processors, further causes the processors to update the first, second, or third positional information to correspond to a same timestamp before determining the first pose and the second pose.

15. The non-transitory computer readable medium of claim 11, wherein the surgical instrument comprises one or more of a robotic arm, an end-effector of the robotic arm, or an object attached to one or more of the robotic arm or the end-effector of the robotic arm.

* * * * *